(12) United States Patent
Nakagawa

(10) Patent No.: US 11,096,564 B2
(45) Date of Patent: Aug. 24, 2021

(54) CURVED TUBE FOR ENDOSCOPE AND METHOD OF MANUFACTURING CURVED TUBE FOR ENDOSCOPE

(71) Applicant: OLYMPUS CORPORATION, Tokyo (JP)

(72) Inventor: Hironori Nakagawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 401 days.

(21) Appl. No.: 16/371,180

(22) Filed: Apr. 1, 2019

(65) Prior Publication Data

US 2019/0223692 A1 Jul. 25, 2019

Related U.S. Application Data

(63) Continuation of application No. PCT/JP2017/036015, filed on Oct. 3, 2017.

(30) Foreign Application Priority Data

Oct. 4, 2016 (JP) .............................. JP2016-196689

(51) Int. Cl.
*A61B 1/00* (2006.01)
*A61B 1/005* (2006.01)
(Continued)

(52) U.S. Cl.
CPC .......... *A61B 1/0057* (2013.01); *A61B 1/0011* (2013.01); *A61B 1/0055* (2013.01);
(Continued)

(58) Field of Classification Search
None
See application file for complete search history.

(56) References Cited

U.S. PATENT DOCUMENTS 5,531,664 A * 7/1996 Adachi ................ A61B 1/0058
600/149

FOREIGN PATENT DOCUMENTS

JP H02-246920 A 10/1990
JP 2001-124261 A 5/2001
(Continued)

OTHER PUBLICATIONS

International Search Report dated Oct. 31, 2017 issued in PCT/JP2017/036015.
(Continued)

*Primary Examiner* — Timothy J Neal
(74) *Attorney, Agent, or Firm* — Scully, Scott, Murphy & Presser, P.C.

(57) ABSTRACT

A curved tube for an endoscope includes: a curved tube body including a locked portion provided on an inner peripheral surface of the curved tube body; an operation wire configured to perform a bending operation of the curved tube body; a pipe member which is press-fitted to the operation wire and is locked to the locked portion of the curved tube body; and particles interposed between an outer peripheral surface of the operation wire and an inner peripheral surface of the pipe member. The particles are higher in hardness than materials forming the operation wire and the pipe member and are buried to dig into the outer peripheral surface of the operation wire and the inner peripheral surface of the pipe member.

7 Claims, 11 Drawing Sheets

(51) Int. Cl.
  *B21F 15/00* (2006.01)
  *B21F 45/00* (2006.01)
  *G02B 23/24* (2006.01)
  *B21K 25/00* (2006.01)

(52) U.S. Cl.
  CPC ............ *B21F 15/00* (2013.01); *B21F 45/008* (2013.01); *B21K 25/00* (2013.01); *G02B 23/24* (2013.01)

(56) References Cited

FOREIGN PATENT DOCUMENTS

| | | |
|---|---|---|
| JP | 2003-204926 A | 7/2003 |
| JP | 2005-177120 A | 7/2005 |
| JP | 2006-080030 A | 3/2006 |
| JP | 2016-116807 A | 6/2016 |

OTHER PUBLICATIONS

Chinese Office Action dated Feb. 19, 2021 received in 201780059338.6.

\* cited by examiner

US 11,096,564 B2

CURVED TUBE FOR ENDOSCOPE AND METHOD OF MANUFACTURING CURVED TUBE FOR ENDOSCOPE

CROSS-REFERENCE TO RELATED APPLICATION

This application is a continuation of PCT International Application No. PCT/JP2017/036015 filed on Oct. 3, 2017 which claims the benefit of priority from Japanese Patent Application No. 2016-196689, filed on Oct. 4, 2016, the entire contents of which are incorporated herein by reference.

BACKGROUND

The present disclosure relates to a curved tube for an endoscope and a method of manufacturing a curved tube for an endoscope.

A known curved tube for an endoscope (hereinafter, simply referred to as the "curved tube" has a structure in which a plurality of node rings is joined by rivets and an operation wire for a bending operation of the node ring is brazed to a node ring at a distal end as illustrated in JP 2003-204926 A, for example. In the curved tube having such a structure, the node rings are joined to be superimposed on each other in a radial direction so that a thickness of the superimposed portion is doubled. Furthermore, the rivets configured to join the node rings protrude to an inner peripheral side and an outer peripheral side of the node rings each, and thus, there is a problem that inner and outer diameters increase.

Therefore, in recent years, a curved tube that can be bent by forming a plurality of slits in the longitudinal direction of a pipe member using the single pipe member made of Nitinol (a nickel-titanium alloy), which is a shape memory alloy, as a material has appeared instead of the above-described node ring structure. In the case of a curved tube having such a structure, there is no superimposed portion and there is no protrusion of the rivet, and thus, it is possible to make the inner and outer diameters smaller than those of the conventional curved tube.

Here, it is necessary to attach the operation wire for the bending operation even when the curved tube is made of Nitinol. However, when the operation wire is brazed as in JP 2003-204926 A, superelasticity which is a characteristic of Nitinol is lost due to the high temperature. Thus, as illustrated in JP 2006-80030 A, for example, a technique of covering a distal end of an operation wire with a pipe member, reducing a diameter of the pipe member by swaging to fix the pipe member to the operation wire, and then, causing the pipe member to be caught by a wire passing portion provided in a curved tube has been tried.

The technique disclosed in JP 2006-80030 A needs to increase a joining length (that is, a length of the pipe member) between the operation wire and the pipe member to some extent in order to obtain necessary joining strength (tensile strength) as a product. However, a length of a portion of the curved tube where the curved tube is not bent (hereinafter, referred to as a "rigid length") becomes longer if the joining length is long, and thus, there is a risk that it is difficult to draw a smooth line at the time of bending the curved tube so that it is difficult to insert the curved tube into an affected part.

SUMMARY

A curved tube for an endoscope according to one aspect of the present disclosure includes: a curved tube body including a locked portion provided on an inner peripheral surface of the curved tube body; an operation wire configured to perform a bending operation of the curved tube body; a pipe member which is press-fitted to the operation wire and is locked to the locked portion of the curved tube body; and particles interposed between an outer peripheral surface of the operation wire and an inner peripheral surface of the pipe member, wherein the particles are higher in hardness than materials forming the operation wire and the pipe member and are buried to dig into the outer peripheral surface of the operation wire and the inner peripheral surface of the pipe member.

A method of manufacturing a curved tube for an endoscope according to another aspect of the present disclosure includes: attaching particles having higher hardness than substances forming the operation wire and the pipe member onto an outer peripheral surface of the operation wire or an inner peripheral surface of the pipe member to perform a bending operation of a curved tube body; arranging the pipe member around the operation wire; reducing a diameter of the pipe member while interposing the particles between the outer peripheral surface of the operation wire and the inner peripheral surface of the pipe member; press-fitting the pipe member to the operation wire; and mounting the operation wire to the curved tube body by locking the pipe member to a locked portion provided on an inner peripheral surface of the curved tube body.

The above and other features, advantages and technical and industrial significance of this invention will be better understood by reading the following detailed description of presently preferred embodiments of the disclosure, when considered in connection with the accompanying drawings.

DETAILED DESCRIPTION

Hereinafter, embodiments of a curved tube for an endoscope and a method of manufacturing a curved tube for an endoscope according to the present disclosure will be described with reference to the drawings. Incidentally, the present disclosure is not limited to the following embodiments, and constituent elements in the following embodiments include those which can be easily replaced by a person skilled in the art or those which are substantially the same.

Configuration of Endoscope

Figure 1:
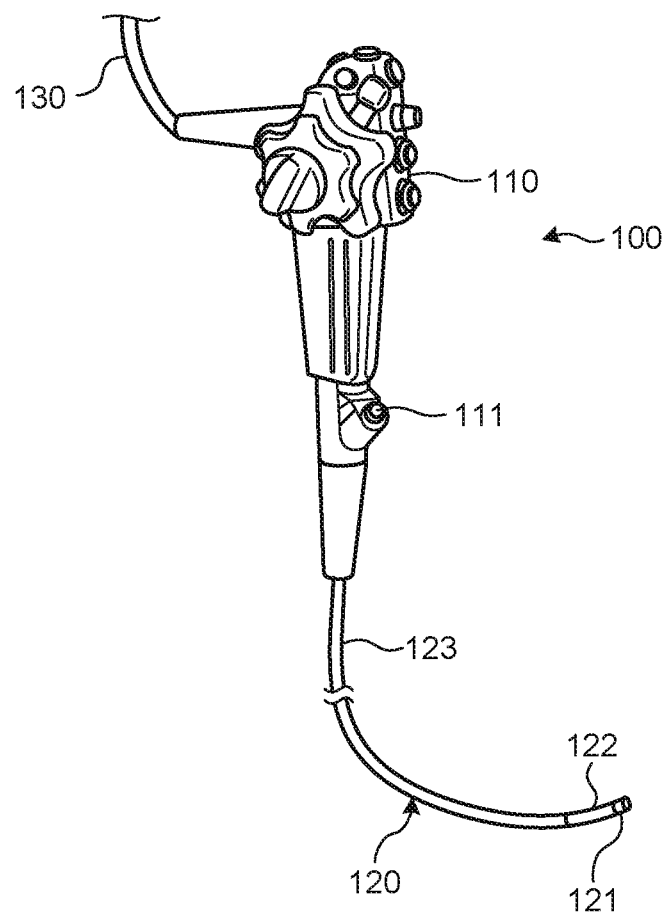
FIG. 1 is a diagram illustrating a configuration of a main part of an endoscope including a curved tube for an endoscope according to an embodiment.

A configuration of an endoscope including a curved tube according to the present disclosure will be described with reference to FIG. 1. As illustrated in FIG. 1, an endoscope 100 includes an operating unit 110, an insertion portion 120, and a universal cord 130.

The operating unit 110 is connected to a proximal end side of the insertion portion 120, and is provided with various buttons and knobs to operate endoscope functions. The operating unit 110 is provided with a treatment tool insertion opening 111 configured to insert a treatment tool, such as biological forceps, an electric scalpel, and an inspection probe, in a body cavity of a subject.

The insertion portion 120 is inserted into the body cavity of the subject during endoscopy, and is constituted by a distal end portion 121, a bent portion 122 connected to a proximal end side of the distal end portion 121, and a flexible tube portion 123 connected to a proximal end side of the bent portion 122.

Specifically, the distal end portion 121 is constituted by a distal end member 2 (see FIG. 2 to be described later) accommodating an imaging module or the like and an outer skin (not illustrated) covering the distal end member 2.

The bent portion 122 is bent by operating a bending operation knob provided in the operating unit 110, and is freely bent in four directions, for example, upward, downward, leftward, and rightward along with the pulling and relaxing of an operation wire 13 (see FIG. 2 described later) inserted through the inside of the bent portion 122. Specifically, the bent portion 122 is constituted by a metal curved tube 1 (see FIG. 2 described later) in which the operation wire 13 and the like are accommodated, and an outer skin (not illustrated) covering the outer periphery of the curved tube 1.

Cables and the like connected to the imaging module or the like built in the distal end portion 121 are provided inside the universal cord 130.

Configuration of Curved Tube

A configuration of the curved tube according to the embodiment will be described with reference to FIGS. 2 and 3. Incidentally, FIG. 2 to be referred to hereinafter illustrates a cross-sectional view of a state where the outer skin is removed from the distal end portion 121 and the bent portion 122 illustrated in FIG. 1. In addition, FIG. 3 is a cross-sectional view of FIG. 2 cut in an X-X direction in which configurations other than a curved tube body 10 to be described below are omitted.

Figure 2:
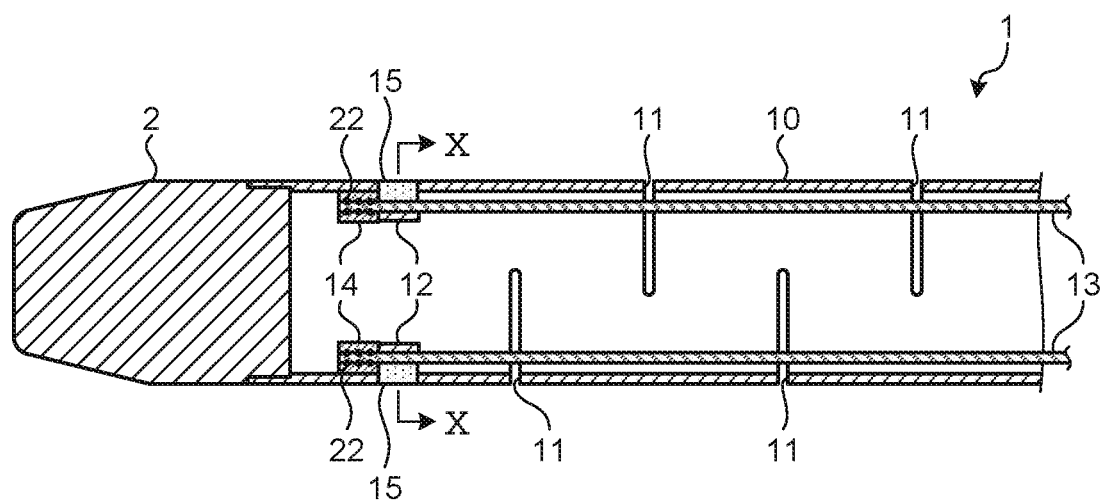
FIG. 2 is a cross-sectional view illustrating a configuration of the curved tube for an endoscope according to the embodiment.
Figure 3:
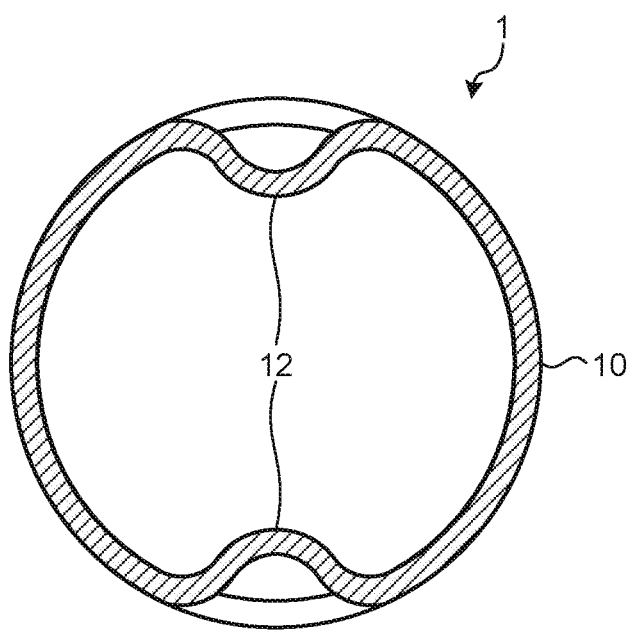
FIG. 3 is a cross-sectional view illustrating a configuration of a curved tube body of the curved tube for an endoscope according to the embodiment.

As illustrated in FIG. 2, the curved tube 1 according to the present embodiment includes the curved tube body 10, the operation wire 13, and a pipe member 14. The curved tube body 10 is made of Nitinol and is formed in a cylindrical shape. In addition, the distal end member 2 is attached to a distal end side of the curved tube body 10.

The imaging module having an imaging optical system and an imaging element, a light guide that irradiates the subject with illumination light, and various channels for insertion of air supply and water supply pipes configured to perform air supply and water supply to the subject are formed on the distal end member 2. However, these various channels do not pass in the cross section illustrated in FIG. 2, and thus, are not illustrated.

The curved tube body 10 is provided with a plurality of slits 11 and a wire passing portion 12. The slits 11 are periodically formed at predetermined intervals along the length direction of the curved tube body 10. In addition, each of the slits 11 is formed with a predetermined length from an outer peripheral surface of the curved tube body 10 toward the center thereof, and the adjacent slits 11 are formed such that formed directions, that is, directions each of which is directed from an opening end of the slit 11 toward a terminal end are opposite to each other. With the plurality of slits 11, the curved tube body 10 is formed in the state of being divided into a plurality of nodes similarly to the conventional curved tube body (see JP 2003-204926 A), and it is possible to bend the curved tube body 10 due to the superelasticity of Nitinol.

The wire passing portion (locked portion) 12 is provided on the inner peripheral surface side of the curved tube body 10. Specifically, a pair of the wire passing portion 12 is formed at symmetrical positions in the radial direction of the curved tube body 10 as illustrated in FIG. 3. In addition, the wire passing portion 12 can be formed by, for example, deforming a part of the curved tube body 10 in a recessed shape from the outer peripheral surface of the curved tube body 10 toward the center, and the recessed amount at that time is set to a recessed amount that enables the operation wire 13 to be inserted therein.

As illustrated in FIG. 2, the operation wire 13 is inserted in each of the pair of wire passing portions 12, and the inside of the recess is filled with an adhesive 15. As a result, the operation wire 13 is bonded and fixed to the wire passing portion 12. In addition, the pipe member 14, which has been press-fitted to the distal end of the operation wire 13, is locked to side surfaces of the pair of wire passing portions 12.

The operation wire 13 is configured to perform the bending operation of the curved tube body 10, and is inserted in each of the pair of wire passing portions 12. The operation wire 13 is made of a substance having Vickers hardness of about 600 and is configured using a twisted wire of metal strands, for example, stainless steel SUS 316 WPL or the like.

The pipe member 14 is configured to lock the operation wire 13 to the curved tube body 10. As illustrated in FIG. 2, the pipe member 14 is press-fitted to the distal end of the operation wire 13 and is locked to the side surface of the wire passing portion 12 of the curved tube body 10. As a result, the pipe member 14 prevents the operation wire 13 from dropping out of the wire passing portion 12.

Here, when the pipe member 14 is simply press-fitted to the operation wire 13, there is a risk that the operation wire 13 slips off from the pipe member 14 to drop out, for example, when a pulling force is applied to both the pipe member 14 and the operation wire 13. Therefore, in the present embodiment, particles 22 are interposed between an outer peripheral surface of the operation wire 13 and an inner peripheral surface of the pipe member 14 as will be described later, thereby preventing the operation wire 13 from dropping out using the anchor effect thereof.

The pipe member 14 is made of a substance having Vickers hardness of about 400, and is made of, for example, stainless steel SUS303 or SUS304, or the like. It is preferable that a difference in Vickers hardness between the pipe member 14 and the operation wire 13 is as small as possible, and, for example, it is preferable that the difference in Vickers hardness between the pipe member 14 and the operation wire 13 is 300 or less. In this manner, each of the pipe member 14 and the operation wire 13 is made of substances whose difference in Vickers hardness is within a predetermined value so that it is possible to cause the particles 22 to dig evenly into both the pipe member 14 and the operation wire 13 in a process of manufacturing the curved tube 1 to be described later.

The particles 22 are interposed between the outer peripheral surface of the operation wire 13 and the inner peripheral surface of the pipe member 14. Incidentally, the particles 22 illustrated in FIG. 2 are drawn in an exaggerated manner for convenience of description, and are different from the actual size.

The particles 22 are made of a substance having higher hardness than the substances forming the operation wire 13 and the pipe member 14, for example, having Vickers hardness of 1000 or more. As the particles 22, for example, diamond particles, corundum (sapphire or ruby) particles made of aluminum oxide $Al_2O_3$, alumina particles used as a polishing agent, or the like can be used. Incidentally, when the particles 22 are made of diamond particles, it is preferable to use the diamond particles having an average particle diameter of 10 to 20 μm.

Here, the pipe member 14 is press-fitted to the distal end of the operation wire 13 as illustrated in FIG. 2 with the particles 22 having higher hardness than the substances forming the operation wire 13 and the pipe member 14 interposed therebetween as illustrated in FIG. 2. Thus, the particles 22 are buried so as to dig into both the outer peripheral surface of the operation wire 13 and the inner peripheral surface of the pipe member 14 while maintaining the original shapes and function as a slip stopper that increases a frictional force between the operation wire 13 and the pipe member 14. Therefore, in the curved tube 1 according to the present embodiment, the operation wire 13 is prevented from dropping out due to the anchor effect by the particles 22 even when the pulling force is applied to the operation wire 13 and the pipe member 14.

Method of Manufacturing Curved Tube (First Embodiment)

A method of manufacturing the curved tube 1 according to a first embodiment will be described with reference to FIGS. 4 to 13. In the method of manufacturing the curved tube 1 according to the present embodiment, an attachment step, an arrangement step, a reciprocation step, a temporary fixing step, a press-fitting step, a cutting step, and a mounting step are performed in this order.

Attachment Step

Figure 4:
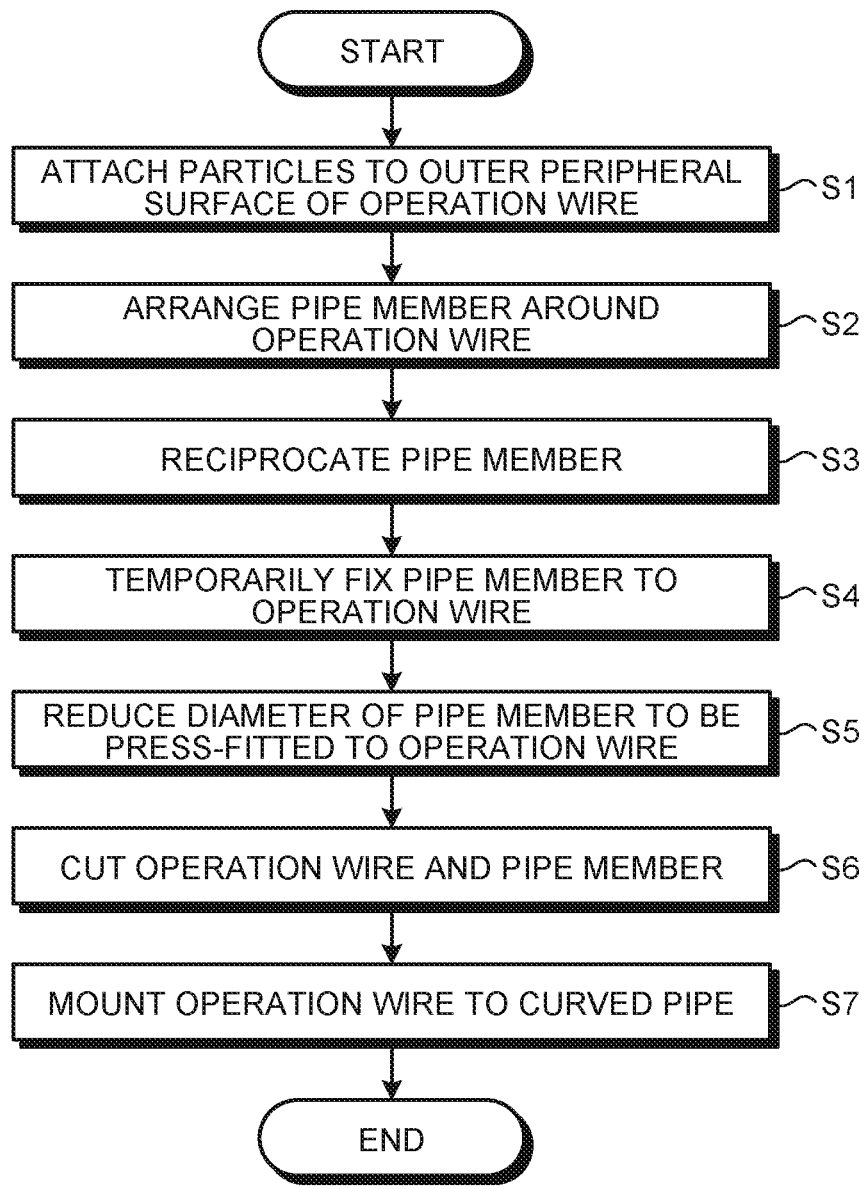
FIG. 4 is a flowchart illustrating a method of manufacturing a curved tube for an endoscope according to a first embodiment.
Figure 5:
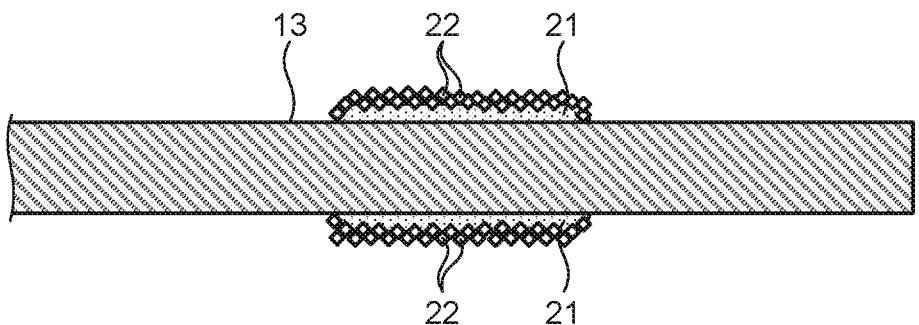
FIG. 5 is a diagram for describing an attachment step of the method of manufacturing the curved tube for an endoscope according to the first embodiment.

In this step, the particles 22 are attached to the outer peripheral surface of the operation wire 13 (Step S1 in FIG. 4). In this step, specifically, an adhesive 21 is applied to a predetermined position of the operation wire 13, and the particles 22 are attached to the application position as illustrated in FIG. 5. Incidentally, it is preferable to use the adhesive 21 which can withstand sterilization performed by a sterilizing device such as STERRAD (registered trademark) and has a workable time of 30 minutes or longer.

In addition, it is preferable to use particles having a particle size of ⅟₁₀ to ½ of a difference between an outer diameter of the operation wire 13 and an inner diameter of the pipe member 14 before performing the press-fitting step, which will be described later, as the particles 22 used in this step. In this manner, as a particle diameter of the particles 22 is set to a size within a predetermined range with respect to the difference between the outer diameter of the operation wire 13 and the inner diameter of the pipe member 14, it is possible to prevent the particles 22 from becoming too large to flow in the reciprocation step to be described later, and further, it is possible to prevent the particles 22 from becoming too small to dig into the operation wire 13 and the pipe member 14 in the press-fitting step to be described later.

Arrangement Step

In this step, the pipe member 14 is arranged around the operation wire 13 (Step S2 in FIG. 4). Specifically, the pipe member 14 is inserted from the distal end side of the operation wire 13 in this step as illustrated in FIG. 6.

Reciprocation Step

In this step, the particles 22 are spread between the operation wire 13 and the pipe member 14 by reciprocating the pipe member 14 with respect to the operation wire 13 (Step S3 in FIG. 4). Specifically, the pipe member 14 is reciprocated between one side (the right side in the drawing) and the other side (the left side in the drawing) of the operation wire 13 in the state of fixing the operation wire 13 in this step as illustrated in FIGS. 6 to 10 so that the particles 22, which has initially attached to the surface of the adhesive 21, are caused to enter the inside of the adhesive 21. Further, such reciprocation is repeated a plurality of times, thereby averaging the density of the particles 22 outside the adhesive 21. Hereinafter, each stage of FIGS. 6 to 10 will be described in detail.

Figure 6:
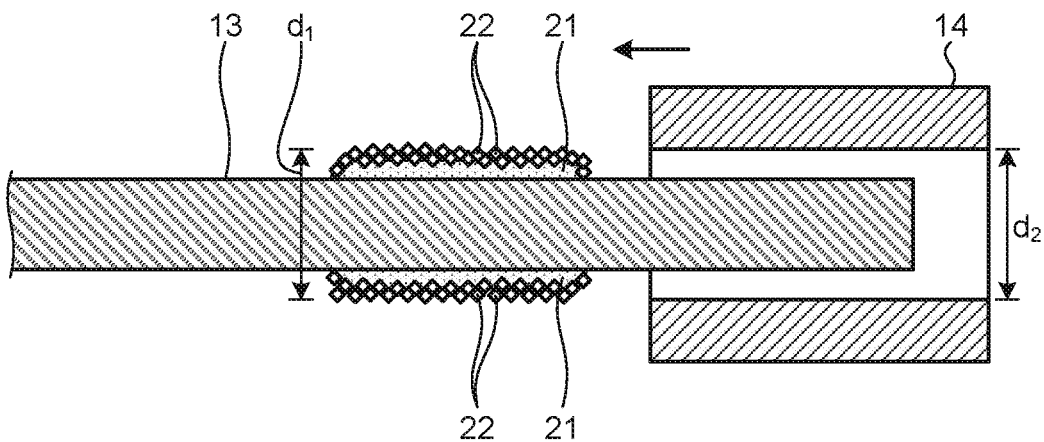
FIG. 6 is a diagram for describing an arrangement step of the method of manufacturing the curved tube for an endoscope according to the first embodiment.
Figure 7:
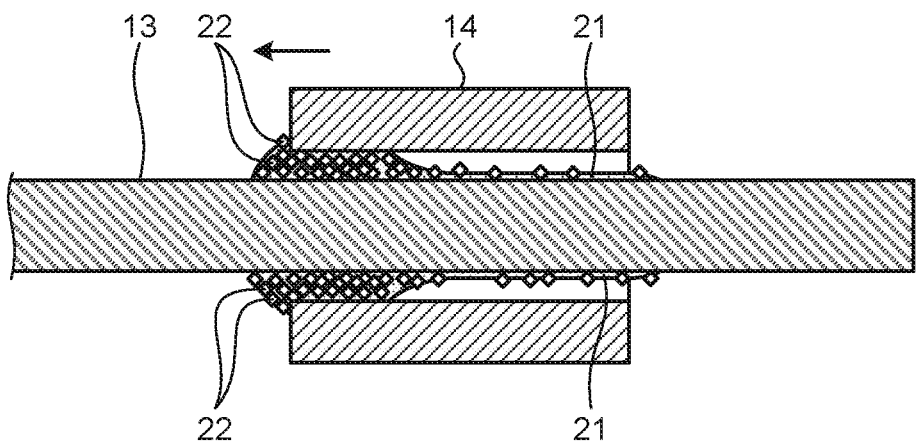
FIG. 7 is a diagram for describing a reciprocation step of the method of manufacturing the curved tube for an endoscope according to the first embodiment.

Here, an outer diameter $d_1$ of a region of the operation wire 13 where the particles 22 are attached is larger than an inner diameter $d_2$ of the pipe member 14 before performing this step as illustrated in FIG. 6. Thus, when the pipe member 14 is moved from one side to the other side of the operation wire 13 as illustrated in FIG. 7, the pipe member 14 comes into contact with the adhesive 21 and the particles 22, the particles 22 enter between the outer peripheral surface of the operation wire 13 and the inner peripheral surface of the pipe member 14 while entering the inside of the adhesive 21.

Figure 8:
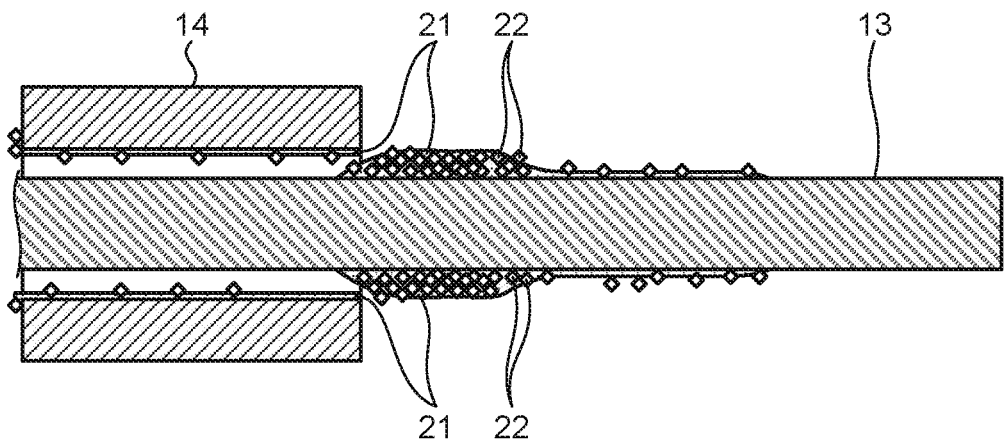
FIG. 8 is a diagram for describing the reciprocation step of the method of manufacturing the curved tube for an endoscope according to the first embodiment.

Further, when the pipe member 14 is further moved as illustrated in FIG. 8, all the particles 22 which have been present a position larger than the inner diameter $d_2$ of the pipe member 14 enter the inside of the adhesive 21, and the outer diameter $d_1$ of the region of the operation wire 13 where the particles 22 are attached becomes equal to or smaller than the inner diameter $d_2$ of the pipe member 14. At this stage, however, the particles 22 are biased to a predetermined position as illustrated in the same drawing.

Figure 9:
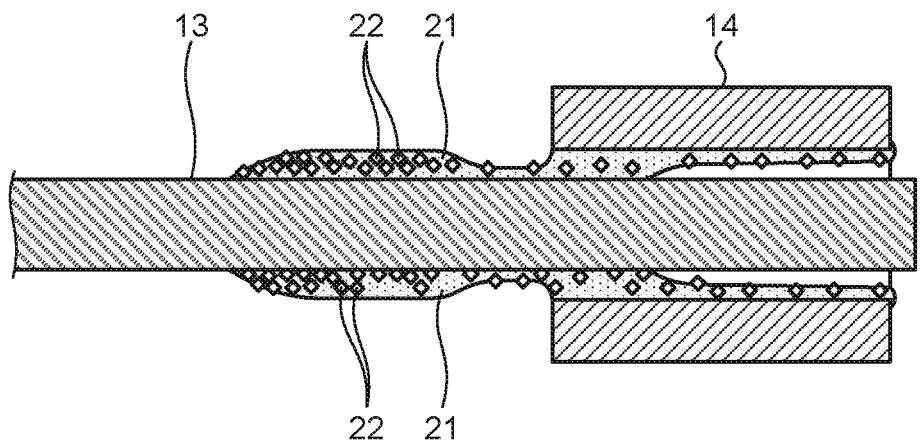
FIG. 9 is a diagram for describing the reciprocation step of the method of manufacturing the curved tube for an endoscope according to the first embodiment.
Figure 10:
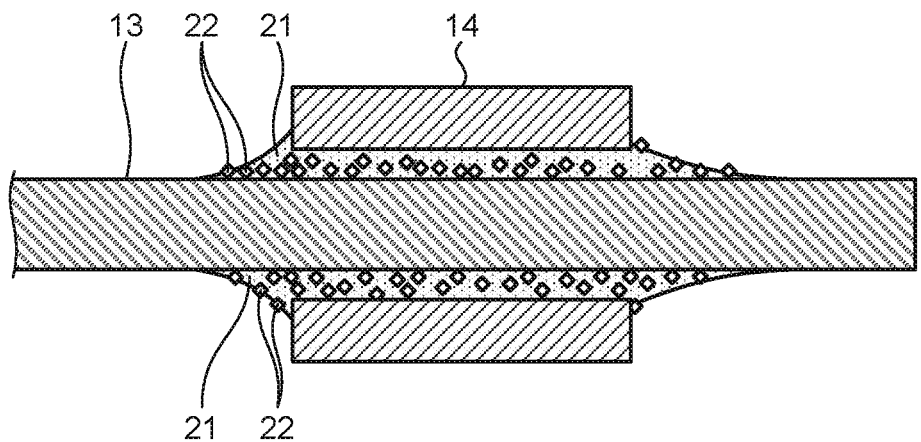
FIG. 10 is a diagram for describing the reciprocation step of the method of manufacturing the curved tube for an endoscope according to the first embodiment.

Therefore, when the pipe member 14 is moved from the other side to the one side of the operation wire 13 this time, the particles 22 move in a direction to move the pipe member 14 due to the viscosity of the adhesive 21 as illustrated in FIG. 9. In this step, such reciprocation (see FIGS. 6 to 9) of the pipe member 14 is repeated a plurality of times, thereby distributing the particles 22 uniformly in a predetermined range on the outer peripheral surface of the operation wire 13 as illustrated in FIG. 10.

Incidentally, the pipe member 14 is reciprocated between one side and the other side of the operation wire 13 in the state of fixing the operation wire 13 in this step, but on the contrary, the operation wire 13 may be reciprocated between one side and the other side of the pipe member 14 in the state of fixing the pipe member 14.

Temporary Fixing Step

Figure 11:
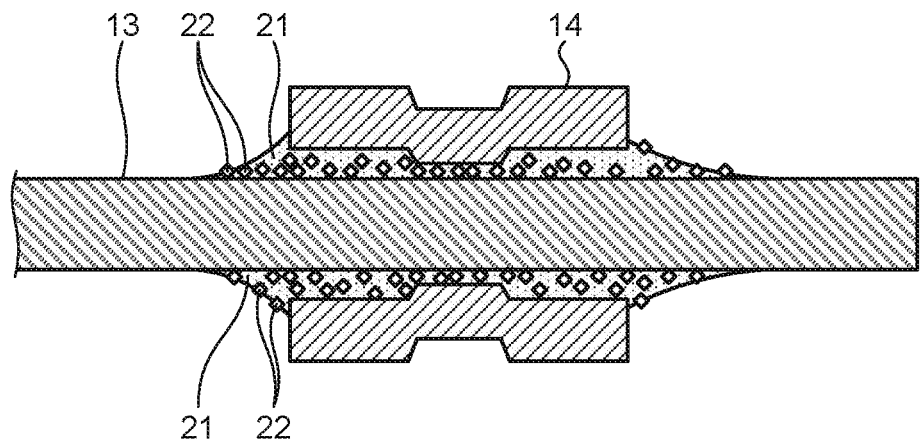
FIG. 11 is a diagram for describing a temporary fixing step of the method of manufacturing the curved tube for an endoscope according to the first embodiment.

In this step, the pipe member 14 is temporarily fixed to the operation wire 13 (Step S4 in FIG. 4). In this step, specifically, a predetermined position of the pipe member 14 in the longitudinal direction is crimped as illustrated in FIG. 11 using a crimping tool (not illustrated). This prevents the pipe member 14 from slipping during a swaging process of the press-fitting step to be described later.

Press-Fitting Step

In this step, the diameter of the pipe member 14 is reduced while interposing the particles 22 between the outer peripheral surface of the operation wire 13 and the inner peripheral surface of the pipe member 14, and the pipe member 14 is press-fitted to the operation wire 13 (Step S5 in FIG. 4). Specifically, in this step, the diameter of the pipe member 14 is reduced using a rotary swaging machine (not illustrated). This rotary swaging machine has a pair of opposing dies in which grooves (recessed portions) each of which has an arcuate cross section that is shallowly tapered, and the operation wire 13 and the pipe member 14 are arranged between the dies. Further, the inner and outer diameters of the pipe member 14 are reduced by advancing and retreating the pair of opposing dies while rotating the dies at a high speed.

Figure 12:
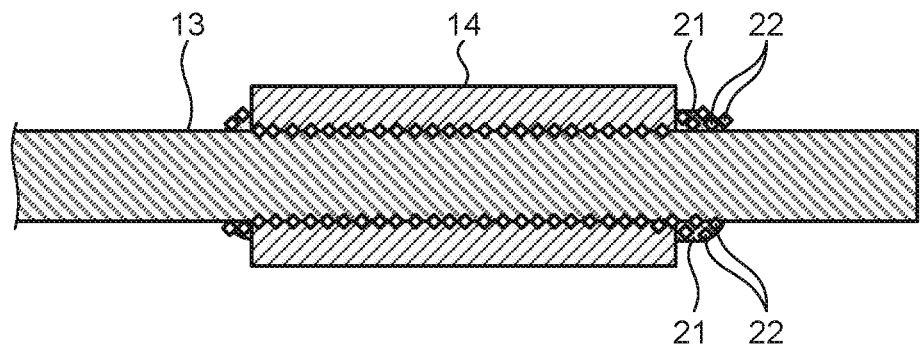
FIG. 12 is a diagram for describing a press-fitting step of the method of manufacturing the curved tube for an endoscope according to the first embodiment.

With such diameter reduction processing, a gap between the operation wire 13 and the pipe member 14 is gradually narrowed, and the operation wire 13 and the pipe member 14 firmly adhere to each other. Further, the particles 22 that have lost a place to proceed digs into a portion between the outer peripheral surface of the operation wire 13 and the inner peripheral surface of the pipe member 14 in the course of narrowing the gap between the operation wire 13 and the pipe member 14, and are completely buried between both the operation wire 13 and the pipe member 14 eventually as illustrated in FIG. 12. Thereafter, ultrasonic cleaning is performed to remove the adhesive 21 and the particles 22 that protrude from the pipe member 14, thereby completing this step.

Cutting Step

Figure 13:
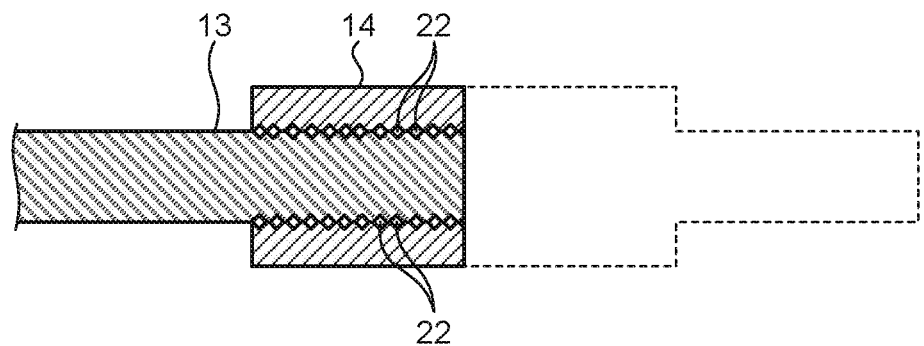
FIG. 13 is a diagram for describing a cutting step of the method of manufacturing the curved tube for an endoscope according to the first embodiment.

In this step, the operation wire 13 and the pipe member 14 are cut (Step S6 in FIG. 4). Specifically, in this step, each end face of the operation wire 13 and the pipe member 14 is scraped by, for example, a belt sander or the like to be processed to a length that provides the necessary joining strength as illustrated in FIG. 13.

Mounting Step

In this step, the operation wire 13 is mounted to the curved tube body 10 by locking the pipe member 14 to the wire passing portion 12 provided on the inner peripheral surface of the curved tube body 10 of the curved tube 1 (Step S7 in FIG. 4). Specifically, in this step, the pipe member 14 is brought into contact with the side surface of the wire passing portion 12 to be locked after the operation wire 13 is inserted into the wire passing portion 12 of the curved tube body 10 as illustrated in FIG. 2 described above. Then, the wire passing portion 12 is filled with the adhesive 15, and the operation wire 13 is bonded and fixed to the wire passing portion 12.

According to the curved tube 1 manufactured by the above-described manufacturing method, the frictional force between the operation wire 13 and the pipe member 14 is increased by causing the particles 22 having predetermined hardness to dig into the outer peripheral surface of the operation wire 13 and the inner peripheral surface of the pipe member 14 so that it is possible to inhibit the slip of the pipe member 14. Therefore, it is possible to obtain a desired joining strength without increasing a joining length between the operation wire 13 and the pipe member 14.

Here, the diameter of the pipe member 14 is reduced to tighten the operation wire 13 in the swaging processing, thereby joining the pipe member 14 and the operation wire 13 by the frictional force. The joining strength at that time is proportional to the joining length between the operation wire 13 and the pipe member 14 (that is, the length of the pipe member 14).

Meanwhile, when the particles 22 having higher hardness than the operation wire 13 and the pipe member 14 are interposed between the operation wire 13 and the pipe member 14 as in the curved tube 1 according to the present embodiment, the particles 22 dig into both of the operation wire 13 and the pipe member 14. In such a state, the frictional force at the time of pulling the operation wire 13 and the pipe member 14 increases by the interposition of the particles 22, and thus, the tensile strength is greatly improved.

In addition, the joining length for obtaining the necessary joining strength as a product in the curved tube 1 according to the present embodiment is shorter than a joining length of the case of joining a pipe member to an operation wire simply by swaging processing as illustrated in JP 2006-80030 A. Therefore, it is possible to shorten a rigid length as compared to the known curved tube, and the insertability into an affected part is improved so that it is possible to reduce a burden on a patient.

Method of Manufacturing Curved Tube (Second Embodiment)

A method of manufacturing a curved tube 1 according to a second embodiment will be described with reference to FIGS. 14 to 17. The adhesive 21 and the particles 22 are applied to the pipe member 14 side in the present embodiment although the adhesive 21 and the particles 22 are applied to the operation wire 13 side in the manufacturing method of the curved tube 1 according to the first embodiment described above.

Even in the method of manufacturing the curved tube 1 according to the present embodiment, an attachment step, an arrangement step, a reciprocation step, a temporary fixing step, a press-fitting step, a cutting step, and a mounting step are performed in this order. Since the temporary fixing step, the press-fitting step, the cutting step, and the mounting step are the same as those in the first embodiment, a detailed description thereof will be omitted.

Attachment Step

Figure 14:
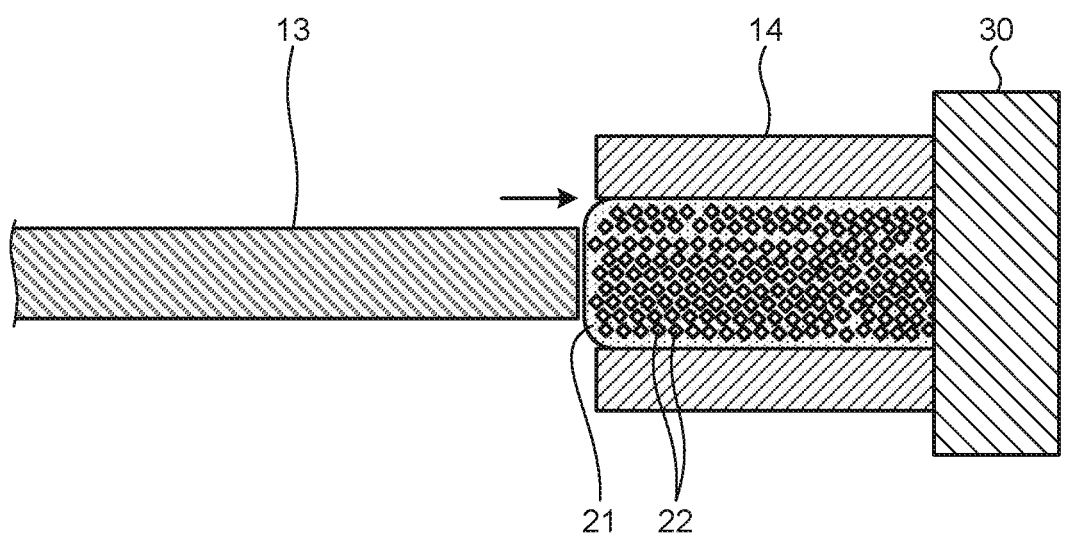
FIG. 14 is a diagram for describing an attachment step and an arrangement step of a method of manufacturing a curved tube for an endoscope according to a second embodiment.

In this step, the particles 22 are attached to the inner peripheral surface of the pipe member 14 as illustrated in FIG. 14. Specifically, in this step, the particles 22 are introduced into the adhesive 21 and stirred by a stirrer or the like (not illustrated) to form a state where the particles 22 are uniformly dispersed in the adhesive 21. Subsequently, a syringe or the like (not illustrated) is filled with the adhesive 21 including the particles 22, and the adhesive 21 including the particles 22 is injected into the pipe member 14. Then, a side opposite to a side on which the operation wire 13 is inserted is covered with a lid member 30 to be blocked as illustrated in FIG. 14.

Arrangement Step

Figure 15:
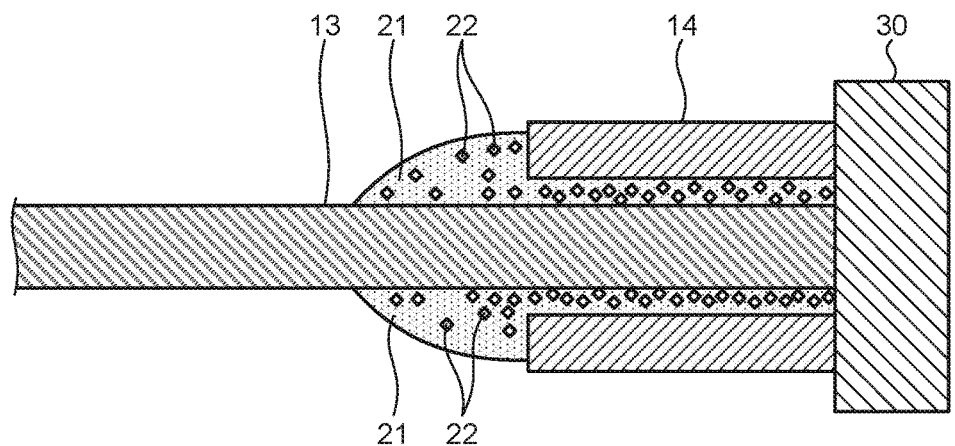
FIG. 15 is a diagram for describing the arrangement step of the method of manufacturing the curved tube for an endoscope according to the second embodiment.

In this step, the operation wire 13 is inserted into the pipe member 14 and brought into contact with the lid member 30 as illustrated in FIG. 15. As a result, the adhesive 21 including the particles 22 is pushed out from a side of the operation wire 13, and the adhesive 21 protrudes to the outside of the pipe member 14. However, at this stage, the number of particles 22 protruding to the outside of the pipe member 14 is smaller than the number of the particles 22 remaining in the pipe member 14.

Reciprocation Step

Figure 16:
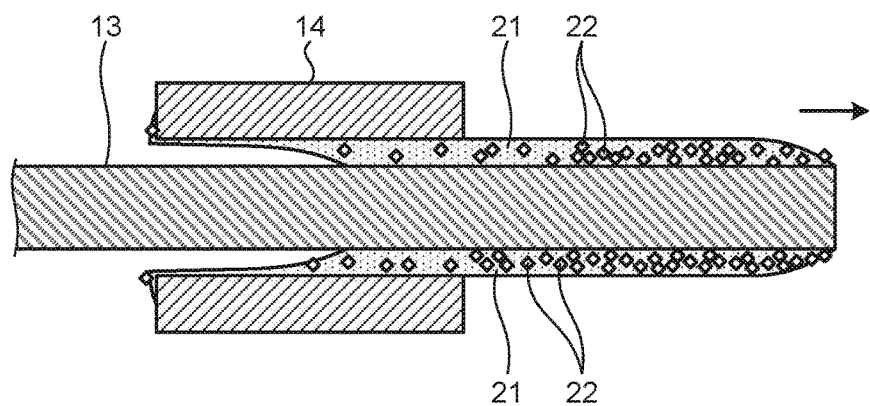
FIG. 16 is a diagram for describing a reciprocation step of the method of manufacturing the curved tube for an endoscope according to the second embodiment.
Figure 17:
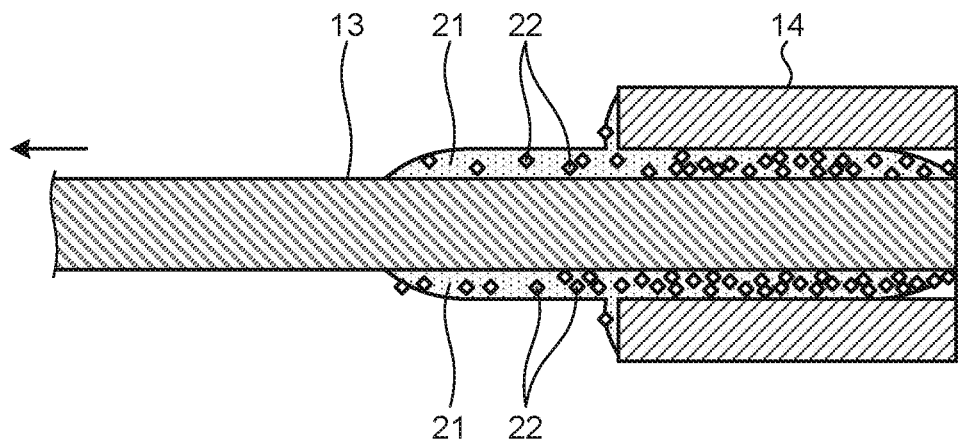
FIG. 17 is a diagram for describing the reciprocation step of the method of manufacturing the curved tube for an endoscope according to the second embodiment.

In this step, the particles 22 are spread between the operation wire 13 and the pipe member 14 by reciprocating the operation wire 13 with respect to the pipe member 14. In this step, specifically, the operation wire 13 is reciprocated between one side (the right side in the drawing) of the pipe member 14 and the other side (the left side in the drawing) in a state where the lid member 30 has been removed and the pipe member 14 has been fixed as illustrated in FIGS. 16 and 17. Then, the density of the particles 22 outside the adhesive 21 is averaged as such reciprocation is repeated a plurality of times, and the particles 22 are uniformly distributed in a predetermined range on the outer peripheral surface of the operation wire 13.

Incidentally, the operation wire 13 is reciprocated between one side and the other side of the pipe member 14 in the state of fixing the pipe member 14 in this step, but on the contrary, the pipe member 14 may be reciprocated between one side and the other side of the operation wire 13 in the state of fixing the operation wire 13.

Subsequently, the temporary fixing step, the press-fitting step, the cutting step, and the mounting step are performed similarly to the above-described first embodiment after this reciprocation step, thereby manufacturing the curved tube 1.

Even with the curved tube 1 manufactured by the manufacturing method described above, it is possible to increase a frictional force between the operation wire 13 and the pipe member 14, and thus, it is possible to obtain a desired joining strength without increasing a joining length between the operation wire 13 and the pipe member 14, which is similar to the above-described first embodiment.

In addition, in the present embodiment, a state where the particles 22 are uniformly dispersed in the adhesive 21 is created, and then, the adhesive 21 including the particles 22 is attached to the inside of the pipe member 14 in the attachment step. As a result, the particles 22 have already been uniformly dispersed in the adhesive 21 to some extent in the stage before performing the reciprocation step as illustrated in FIG. 14 as compared to the above-described first embodiment (see FIG. 6). Therefore, the number of times of reciprocation in the reciprocation step can be reduced as compared with the first embodiment, and the manufacturing time can be shortened. In addition, it is also possible to automate the attachment step by using the stirrer, the syringe, or the like in the present embodiment although it is necessary to manually, for example, perform the attachment step in the first embodiment.

Method of Manufacturing Curved Tube (Third Embodiment)

A method of manufacturing a curved tube according to a third embodiment will be described with reference to FIGS. 18 and 19. An operation wire 13A and a pipe member 14A are made of tungsten having higher hardness than stainless steel in the present embodiment although both the operation wire 13 and the pipe member 14 are made of stainless steel in the methods of manufacturing the curved tube 1 according to the first and second embodiments. In addition, the operation wire 13A and the pipe member 14A have the same Vickers hardness in the present embodiment.

In the method of manufacturing the curved tube according to the present embodiment, an attachment step, an arrangement step, a reciprocation step, a temporary fixing step, a heating step, a press-fitting step, a cutting step, and a mounting step are performed in this order. Since the attachment step, the arrangement step, the reciprocation step, the temporary fixing step, the cutting step, and the mounting step are the same as those in the first and second embodiments, a detailed description thereof will be omitted.

Heating Step

Figure 18:
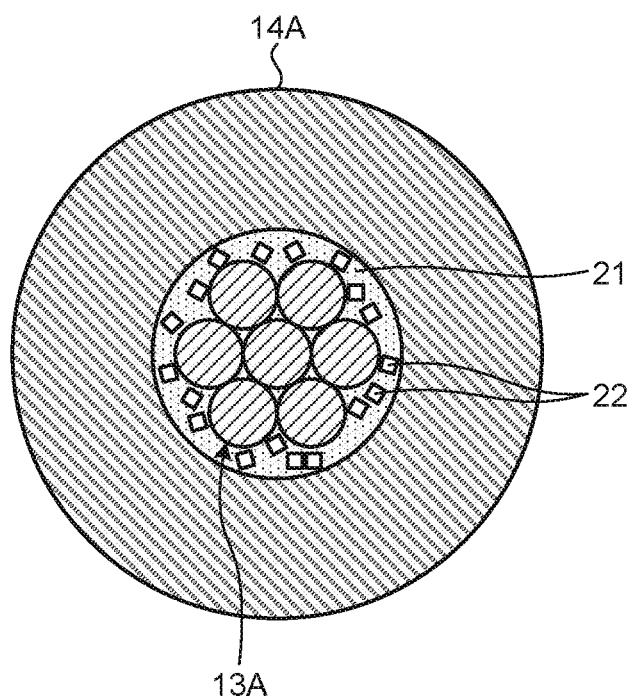
FIG. 18 is a diagram for describing a method of manufacturing a curved tube for an endoscope according to a third embodiment.
Figure 19:
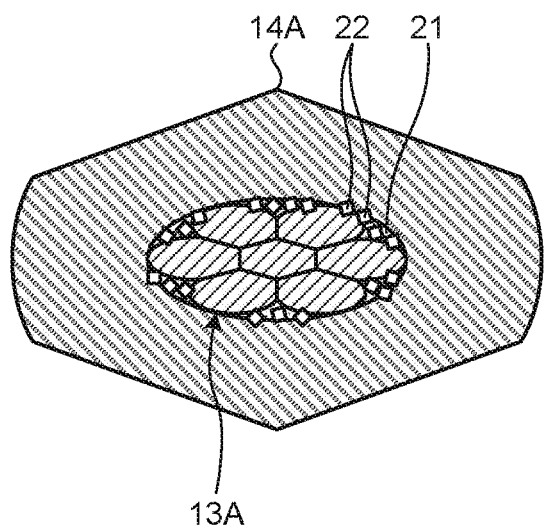
FIG. 19 is a diagram for describing the method of manufacturing the curved tube for an endoscope according to the third embodiment.

Through the attachment step, the arrangement step, the reciprocation step, and the temporary fixing step, a state where the particles 22 are uniformly distributed between an outer peripheral surface of the operation wire 13A and an inner peripheral surface of the pipe member 14A is formed as illustrated in FIG. 18. In the heating step, the pipe member 14A in such a state is heated so as to be equal to or higher than a brittle-ductile transition temperature of tungsten.

Press-Fitting Step

In this step, the pipe member 14A and the operation wire 13A are set in a press machine (not illustrated), and the pipe member 14A is crushed by a punch (not illustrated). As a result, a gap between the inner peripheral surface of the pipe member 14A and the outer peripheral surface of the operation wire 13A is eliminated, and the particles 22 that have lost a place to proceed digs into a portion between the outer peripheral surface of the operation wire 13A and the inner peripheral surface of the pipe member 14A and are buried between both the operation wire 13A and the pipe member 14A as illustrated in FIG. 19. Thereafter, ultrasonic cleaning is performed to remove the adhesive 21 and the particles 22 that protrude from the pipe member 14A, thereby completing this step.

Subsequently, the curved tube 1 is manufactured by the cutting step and the mounting step are performed similarly to the above-described first and second embodiments after this press-fitting step, thereby manufacturing the curved tube 1.

Even with the curved tube 1 manufactured by the manufacturing method described above, it is possible to increase a frictional force between the operation wire 13A and the pipe member 14A, and thus, it is possible to obtain a desired joining strength without increasing a joining length between the operation wire 13A and the pipe member 14A, which is similar to the first and second embodiments.

In addition, the tungsten operation wire 13A having strength about twice as high as strength of the stainless steel operation wire 13 is used in the present embodiment. Therefore, it is possible to set a wire diameter of the operation wire 13A to be about ⅔ of that of the stainless steel operation wire 13, for example, and thus, it is possible to secure a wider space inside the curved tube body 10.

The curved tube for the endoscope and the method of manufacturing the curved tube for the endoscope according to the present disclosure have been more specifically described with the modes for carrying out the invention as above, the gist of the present invention is not limited to these descriptions but needs to be broadly interpreted based on the description of the claims. In addition, it is a matter of course that various modifications and alterations based on these descriptions are included in the gist of the present invention.

For example, the particles 22 are attached to the adhesive 21 applied to the outer peripheral surface of the operation wire 13 in the attachment step of the method of manufacturing the curved tube 1 according to the first embodiment, but the adhesive 21 including the particles 22 may be attached to the outer peripheral surface of the operation wire 13 after creating the state where the particles 22 are uniformly dispersed in the adhesive 21 similarly to the above-described second embodiment.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A curved tube for an endoscope, comprising:
   a curved tube body including a locked portion provided on an inner peripheral surface of the curved tube body;
   an operation wire configured to perform a bending operation of the curved tube body;
   a pipe member which is press-fitted to the operation wire and is locked to the locked portion of the curved tube body; and
   particles interposed between an outer peripheral surface of the operation wire and an inner peripheral surface of the pipe member,
   wherein the particles are higher in hardness than materials forming the operation wire and the pipe member and are buried to dig into the outer peripheral surface of the operation wire and the inner peripheral surface of the pipe member.

2. The curved tube for an endoscope according to claim 1, wherein the particles have Vickers hardness of 1000 or more.

3. The curved tube for an endoscope according to claim 1, wherein a difference in Vickers hardness between the operation wire and the pipe member is 300 or less.

4. A method of manufacturing a curved tube for an endoscope, the method comprising:
   attaching particles having higher hardness than substances forming the operation wire and the pipe member onto an outer peripheral surface of the operation wire or an inner peripheral surface of the pipe member to perform a bending operation of a curved tube body;
   arranging the pipe member around the operation wire;
   reducing a diameter of the pipe member while interposing the particles between the outer peripheral surface of the operation wire and the inner peripheral surface of the pipe member;
   press-fitting the pipe member to the operation wire; and
   mounting the operation wire to the curved tube body by locking the pipe member to a locked portion provided on an inner peripheral surface of the curved tube body.

5. The method of manufacturing a curved tube for an endoscope according to claim 4, further comprising reciprocating at least one of the operation wire and the pipe member between the arrangement of the pipe member around the operation wire and the press-fitting of the pipe member to the operation wire to spread the particles between the operation wire and the pipe member.

6. The method of manufacturing a curved tube for an endoscope according to claim 4, wherein the particles have Vickers hardness of 1000 or more.

7. The method of manufacturing a curved tube for an endoscope according to claim 4, wherein a particle diameter of the particles is ⅒ to ½ of a difference between an outer diameter of the operation wire and an inner diameter of the pipe member before the press-fitting of the pipe member to the operation wire.

* * * * *